United States Patent
Umbricht et al.

(10) Patent No.: US 6,726,730 B2
(45) Date of Patent: Apr. 27, 2004

(54) 7-NITRO-2,1,3-BENZOXADIAZOLE DERIVATIVES AND 7-NITRO,2,1,3-BENZTHIADIAZOLE DERIVATIVES AND DYES, WHICH CONTAIN THESE COMPOUNDS AND WHICH ARE USED FOR DYING KERATIN FIBERS

(75) Inventors: Gisela Umbricht, Marly (CH); Hans-Juergen Braun, Ueberstorf (CH); Sylviane Oberson, Ecuvillens (CH); Catherine Mueller, Marly (CH)

(73) Assignee: Wella Aktiengesellschaft, Darmstadt (DE)

( * ) Notice: Subject to any disclaimer, the term of this patent is extended or adjusted under 35 U.S.C. 154(b) by 0 days.

(21) Appl. No.: 10/276,140

(22) PCT Filed: Nov. 6, 2001

(86) PCT No.: PCT/EP01/12806

§ 371 (c)(1),
(2), (4) Date: Nov. 12, 2002

(87) PCT Pub. No.: WO02/076961

PCT Pub. Date: Oct. 3, 2002

(65) Prior Publication Data

US 2003/0171594 A1 Sep. 11, 2003

(30) Foreign Application Priority Data

Mar. 21, 2001 (DE) .......................... 101 13 699

(51) Int. Cl.⁷ ............................... A61K 7/13
(52) U.S. Cl. ............ 8/405; 8/406; 8/408; 8/415; 8/421; 548/125
(58) Field of Search ............ 548/125; 8/405, 8/406, 408, 415, 421

(56) References Cited

U.S. PATENT DOCUMENTS 5,705,649 A    1/1998  Shultz

FOREIGN PATENT DOCUMENTS

EP    0 861 835 A    9/1998

OTHER PUBLICATIONS

Kind, J., et al: "Preparation of 4–(2,–Aryl–2–Oxo–Ethylidene) . . . " J. Prakt. Chem./Chem.–ZTG, 1994, 336(5), 439–43.

Halle et al: "Nucleophilic Displacement of Hydrogen in 4,6–Dinitro–Benzofuran . . . " Tetrahedron Letters, Bd. 26, Nr. 10, 1985, pp. 1307–1310.

Pesin et al: :Synthesis and Properties . . . Journal of General Chemistry of the USSR (English Translation), Bd. 34, 1964, pp. 1270–1273.

*Primary Examiner*—Deborah C. Lambkin
*Assistant Examiner*—Robert Shiao
(74) *Attorney, Agent, or Firm*—Michael J. Striker

(57) ABSTRACT

The new 7-nitro-2,1,3-benzoxadiazole compounds and 7-nitro-2,1,3-benzthiadiazole compounds of formula (I) are:

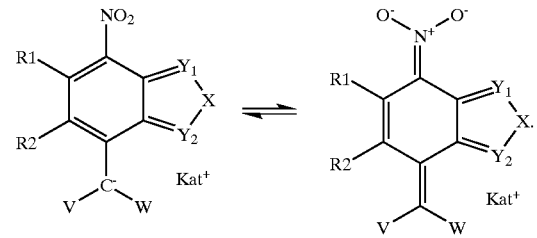

Dyeing agents for keratin fibers containing these compounds and methods of dyeing hair with the dyeing agents are described.

9 Claims, No Drawings

7-NITRO-2,1,3-BENZOXADIAZOLE DERIVATIVES AND 7-NITRO,2,1,3-BENZTHIADIAZOLE DERIVATIVES AND DYES, WHICH CONTAIN THESE COMPOUNDS AND WHICH ARE USED FOR DYING KERATIN FIBERS

This application is a 371 of PCT/EP01/12806 filed on Nov. 6, 2001.

BACKGROUND OF THE INVENTION

The object of the present invention are new 7-nitro-2,1,3-benzoxadiazole or 7-nitro-2,1,3-benzthiadiazole derivatives and dyeing agents for keratin fibers, especially human hair, containing these compounds.

For the color-changing treatment of keratin-containing fibers, such as human hair, wool or fur, two dyeing methods are generally employed. In the first method, the dyeing is produced with so-called oxidative or permanent dyeing agents using a mixture of different developer and coupler substances and an oxidizing agent. If necessary, so-called substantive (non-oxidative) dyes may be added to round off the dyeing result or to produce special color effects. The second method makes use exclusively of substantive dyes, which are applied on the fibers in a suitable carrier composition. This method is easily employed, very mild and distinguished by little damage to the keratin fibers. The substantive dyes, used here, must satisfy a plurality of requirements. They must be safe from toxicological and dermatological points of view and make it possible to achieve dyeings of the desired intensity. Among other things, this also presupposes an adequate solubility in water. In addition, the dyeings achieved are expected to have a good light fastness, acid fastness, crocking resistance and good stability when washed.

As a rule, a combination of different, non-oxidative dyeing agents are required for substantive (non-oxidative) dyes for keratin fibers. Since the selection of red and blue dyes, which can be used in dyeing agents for keratin fibers, is limited, there continues to be a need for such dyes.

SUMMARY OF THE INVENTION

The object of the present invention therefore are new 7-nitro-2,1,3-benzoxadiazole oxadiazole compounds and 7-nitro-2,1,3-benzthiadiazole compounds of formula (I)

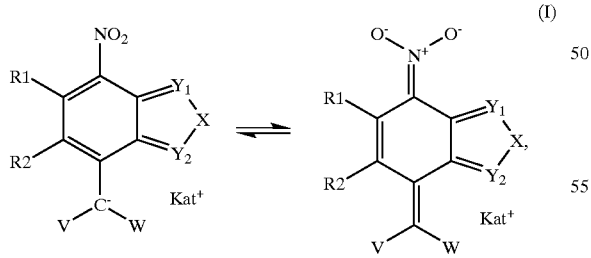

wherein X is oxygen or sulfur;
Y1 and Y2 are the same or different and, independently of one another, each represent a nitrogen atom or a nitrogen monoxide group;
R1 and R2 are the same or different and, independently of one another, each represent hydrogen, a halogen atom (F, Cl, Br, I), a $(C_1-C_4)$-alkyl group, a substituted $(C_1-C_4)$-alkyl group substituted with a halogen atom, a $(C_1-C_4)$-alkoxy group, a nitro group or an $NR^aR^b$ group, the $R^a$ and $R^b$ are the same or different and, independently of one another, each represent hydrogen, a $(C_1-C_4)$-alkyl group, an optionally substituted, aromatic carbocyclic group or a $(C_1-C_4)$-alkane carbonyl group, or $R^a$ and $R^b$, together with the nitrogen atom, form a heterocyclic $(C_3-C_6)$-group;

V represents hydrogen, an aliphatic group, an aromatic isocyclic group, an aromatic heterocyclic group, a cyano group or a carbonyl function (CO)—R3, wherein R3 represents hydrogen, a hydroxy group, a $(C_1-C_4)$-alkoxy group, an amino group, a $(C_1-C_4)$-alkylamino group, a $(C_1-C_6)$-alkyl group or an aryl group;

W represents a cyano group or a carbonyl function (CO)—R4, R4 representing hydrogen, a hydroxy group, a $(C_1-C_4)$-alkoxy group, an amino group, a $(C_1-C_4)$-alkylamino group, a $(C_1-C_6)$-alkyl group or an aryl group; alternatively, V and W together form an aliphatic or aromatic isocyclic or heterocyclic ring system; and Kat⁺ represents an alkali cation, an alkaline earth cation, a quaternary ammonium group, a quaternary phosphonium group or a sulfonium group.

All other tautomeric forms of the general Formula (I) are also included.

Preferred are compounds of Formula (I), in which

X is oxygen or sulfur,

Y1 and Y2 may be the same or different and, independently of one another, represent nitrogen or a nitrogen monoxide group (NO), R1 and R2 may be the same or different and, independently of one another, represent hydrogen, a halogen atom (F, Cl, Br, I), a (C1–C4) alkyl group or a nitro group, V is hydrogen, an aliphatic group, an aromatic isocyclic group, an aromatic heterocyclic group, a cyano group or a carbonyl function (CO)—R3, R3 being hydrogen, a hydroxy group, a $(C_1-C_4)$ alkoxy group, an amino group, a $(C_1-C_4)$ alkylamino group, a $(C_1-C_6)$ alkyl group or an aryl group, W represents a cyano group or a carbonyl function (CO)—R4, R4 being hydrogen, a hydroxy group, a $(C_1-C_4)$ alkoxy group, an amino group, a $(C_1-C_4)$ alkylamino group, a $(C_1-C_6)$ alkyl group or an aryl group; alternatively, V and W may also jointly form an aliphatic or aromatic isocyclic or heterocyclic ring system and Kat⁺ corresponds to an alkali cation, an alkaline earth cation, a quaternary ammonium group, a quaternary phosphonium group or a sulfonium group.

Especially preferred 7-nitro-2,1,3-benzoxadiazole derivatives of Formula (I) are the sodium salt of 4-(dicyanomethyl)-7-nitro-2,1,3-benzoxadiazole, the sodium salt of 4-(1-cyano-2-ethoxy-2-oxoethyl)-7-nitro-2,1,3-benzoxadiazole, the sodium salt of 4-(dicyanomethyl)-7-nitro-2,1,3-benzoxadiazole-N-oxide, the sodium salt of 4-(dihydro-2,4,6(1H,5H)-pyrimidine-trione-5-yl)-7-nitro-2,1,3-benzoxadiazole, the sodium salt of 4-(1-cyano-3,3-dimethyl-2-oxobutyl)-7-nitro-2,1,3-benzoxadiazole, the sodium salt of 4-(bis(methoxycarbonyl)-7-nitro-2,1,3-benzoxadiazole, the sodium salt of 4-(4,5-dihydro-3-methyl-1-phenyl-1H-pyrazole-5-one-4-yl)-7-nitro-2,1,3-benzoxadiazole, the sodium salt of 4-(cyano-(4- nitrophenyl)-methyl)-7-nitro-2,1,3-benzoxadiazole, the sodium salt of 4-((aminocarbonyl)-cyano-methyl)-7-nitro-2,1,3-benzoxadiazole-1-oxide, the sodium salt of 4-(1-cyano-2-ethoxy-2-oxoethyl)-7-nitro-2,1,3-benzoxadiazole-1-oxide, the sodium salt of 4-(1,3-cyclohexane-dione-2-yl)-7-nitro-2,1,3-benzoxadiazole, the sodium salt of 4-(carboxy-cyanomethyl)-7-nitro-2,1,3-benzoxadiazole, the sodium salt of 4-(2-ethoxy-1-nitro-2-oxoethyl)-7-nitro-2,1,3-benzoxadiazole, the sodium salt of 4-((aminocarbonyl)cyanomethyl)-7-nitro-2,1,3-benzoxadiazole,the sodium salt of 4-(dihydro-2-thioxo-4,6(1H,5H)-pyrimidine-dione-5-yl)-7-nitro-2,1,3-benzoxadiazole-1-oxide, the sodium salt of 4-(1,3-dioxo-indan-2-yl)-7-nitro-2,1,3-benzoxadiazole, the sodium salt of 4-(2-oxo-2,3-dihydro-1H-indole-3-yl)-7-nitro-2,1,3-benzoxadiazole, the sodium salt of 4-(4-oxo-2-thioxo-thiazolidine-5-yl)-7-nitro-2,1,3-benzoxadiazole, the sodium salt of 4-(dihydro-6-thioxo-2,4-(1H, 5H)-pyrimidine-dione-3-yl)-7-nitro-2,1,3-benzoxadiazole, the sodium salt of 4-(1-cyano-2-oxo-2-phenylethyl)-2,1,3-benzoxadiazole and the sodium salt of 4-(cyano-(2-nitrophenyl)-methyl)-7-nitro-2,1,3-benzoxadiazole.

Especially preferred 7-nitro-2,1,3-benzthiadiazole derivative of Formula (I) are the sodium salt of 4-(dicyanomethyl)-7-nitro-2,1,3-benzthiadiazole, the sodium salt of 4-(1-cyano-2-ethoxy-2-oxoethyl)-7-nitro-2,1,3-benzthiadiazole, the sodium salt of 4-(cyano-(4-nitrophenyl)-methyl)-7-nitro-2,1,3-benzthiadiazole, the sodium salt of 4-(dicyanomethyl)-7-nitro-2,1,3-benzthiadiazole-N-oxide, the sodium salt of 4-(dihydro-2,4,6(1H,5H)-pyrimidine-trione-5-yl)-7-nitro-2,1,3-benzthiadiazole, the sodium salt of 4-(1-cyano-3,3-dimethyl-2-oxobutyl)-7-nitro-2,1,3-benzthiadiazole, the sodium salt of 4-(bis(methoxycarbonyl)-7-nitro-2,1,3-benzthiadiazole, the sodium salt of 4-(4,5-dihydro-3-methyl-1-phenyl-1H-pyrazole-5-one-4-yl)-7-nitro-2,1,3-benzthiadiazole, the sodium salt of 4-(1,3-cyclohexane-dione-2-yl)-7-nitro-2,1,3-benzthiadiazole, the sodium salt of 4-(carboxy-cyanomethyl)-7-nitro-2,1,3-benzthiadiazole, the sodium salt of 4-(2-ethoxy-1-nitro-2-oxoethyl)-7-nitro-2,1,3-benzthiadiazole, the sodium salt of 4-((aminocarbonyl)cyanomethyl)-7-nitro-2,1,3-benzthiadiazole, the sodium salt of 4-(dihydro-2-thioxo-4,6(1H,5H)-pyrimidine-dione-5-yl)-7-nitro-2,1,3-benzthiadiazole-1-oxide, the sodium salt of 4-(1,3-dioxo-indan-2-yl)-7-nitro-2,1,3-benzthiadiazole, the sodium salt of 4-(2-oxo-2,3-dihydro-1H-indole-3-yl)-7-nitro-2,1,3-benzthiadiazole, the sodium salt of 4-(4-oxo-2-thioxo-thiazolidine-5-yl)-7-nitro-2,1,3-benzthiadiazole, the sodium salt of 4-(dihydro-6-thioxo-2,4-(1H,5H)-pyrimidine-dione-3-yl)-7-nitro-2,1,3-benzthiadiazole, the sodium salt of 4-(1-cyano-2-oxo-2-phenylethyl)-2,1,3-benzthiadiazole and the sodium salt of 4-(cyano-(2-nitrophenyl)-methyl)-7-nitro-2,1,3-benzthiadiazole.

In analogy to the examples, the compounds of Formula (I) can be synthesized easily by a one-step reaction of nitro-substituted benzofuran or their thia analogues with CH active compound according to the following equation:

Equation 1

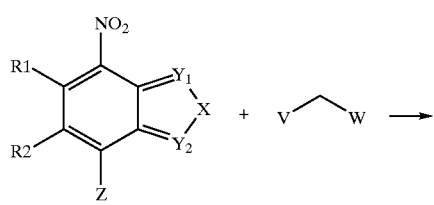

-continued

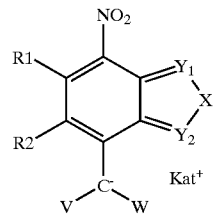

in which R1, R2, X, Y1, Y2, V and W have the meanings given above for Formula (I) and Z represents a hydrogen atom, a halogen atom (F, Cl, Br, I) or an alkoxy group (methoxy, ethoxy) group.

Not only are the new dye derivatives of Formula (I) readily soluble in water, they are also distinguished by a uniform absorption behavior and high washing stability. The inventive dyes enable not only keratin fibers, especially human hair, but also wool and fur to be dyed under gentle and skin-compatible conditions.

A further object of the present invention therefore is the use of compounds of Formula (I) as dye in dyeing agents for keratin fibers, especially in hair-dyeing agents.

A further object of the present invention is an agent for dyeing keratin fibers, especially human hair, which contains at least one compound of the general Formula (I) in a suitable cosmetic base.

The compounds of Formula (I) are used in the inventive dyeing agent preferably in amounts of 0.01 to 10% by weight, an amount of about 0.1 to 8% by weight being particularly preferred.

Especially if it is a hair dyeing agent, the dyeing agent may be in the form of an aqueous or aqueous-alcoholic solution, a cream, a gel, an emulsion or an aerosol foam, the hair dyeing agent being produced in the form of a 1-component preparation, as well as in the form of a multicomponent preparation such as a 2-component preparation, for which the dye derivative of Formula (I) is packaged separately from the remaining components and the ready-for-use hair dyeing agent is prepared only immediately before use by mixing the two components.

Aside from water, the dyeing agent may also contain organic solvents, such as aliphatic or aromatic alcohols, such as ethanol, isopropanol, 1,2-propylene glycol, 1-methoxypropan-2-ol, 1-ethoxy-propan-2-ol, diethylene glycol monomethyl ether or diethylene glycol monoethyl ether, benzyl alcohol, benzyl oxyethanol, phenyl ethyl alcohol, phenoxy ethanol, cinnamyl alcohol and glycol ether, especially ethanol, isopropanol or benzyl alcohol, the water content usually being about 25 to 95% by weight and preferably about 30 to 85% by weight, while the content of organic solvent or a mixture of organic solvents is about 5 to 30% by weight.

Furthermore, the dyeing agent may contain additives, which are known and conventionally used for such preparations, such as perfume oils, complexing agents, waxes, preservatives, thickeners, alginates, guar gum, hair care substances, such as lanolin derivatives, or anionic, nonionic or amphoteric surface active substances. Preferably, amphoteric or nonionic surface active substances, such as betaine surfactants, propionates and glycinates, such as coconut amphoteric glycinates or coconut amphoteric diglycinates, ethoxylated surfactants with 1 to 1000 ethylene oxide units and preferably 1 to 300 ethylene units, such as glyceride alkoxylates, for example, castor oil ethoxylated with 25 ethylene oxide units, polyglycolamides, ethoxylated alcohols and ethoxylated fatty alcohols and ethoxylated fatty acid sugar esters, especially ethoxylated fatty acid esters of sorbitol, are used. The aforementioned components are used in amounts, which are customary for such purposes. For example, the surface-active substances are used in a concentration of 0.1 to 30% by weight and the care materials in an amount of 0.1 to 5% by weight.

Depending on the dyeing shade desired, the dyeing agent may additionally contain, aside from the dyes of Formula (I), further known, substantive dyes from the group of anionic, cationic, nonionic or amphoteric dyes, nitro dyes, azo dyes, anthraquinone dyes and dispersion dyes, these dyes being used individually or in admixture with one another.

The above-named, additional, substantive dyes may be contained in a total amount of about 0.01 to 4% by weight, the total content of dyes in the inventive dyeing agent preferably being about 0.01 to 10% by weight and particularly 0.1 to 5% by weight.

The dyeing agent has a pH of about 3 to 10 and preferably of 4 to 10. Depending on the pH desired, either organic or inorganic acids or organic or inorganic bases are used to adjust the pH.

As suitable acids, especially the following acids are named: α-hydroxycarboxylic acids such as glycolic acid, lactic acid, tartaric acid, citric acid, malic acid, ascorbic acid, gluconic acid lactone, acetic acid, hydrochloric acid or sulfonic acid, as well as mixtures of these acids, are used.

As suitable bases, in particular, sodium carbonate, sodium hydrogen carbonate, potassium carbonate, potassium hydrogen carbonate, sodium phosphate, borax ($Na_2B_4O_7 \times 10\ H_2O$), disodium hydrogen phosphate, alkanolamines, for example, monoethanolamine or triethanolamine, ammonia, amino methyl propanol and sodium hydroxide, as well as mixtures of these bases, may be named.

The dyeing agents, described above, may furthermore contain natural or synthetic polymers or modified polymers of natural origin, customary for cosmetic purposes, a consolidation of the hair being achieved simultaneously with the dyeing. Such agents are generally referred to as shade strengtheners or color strengtheners Of the synthetic polymers known for this purpose, polyvinyl-pyrrolidone, polyvinyl acetate, polyvinyl alcohol or polyacrylic compounds, such as polyacrylic acid or polymethacrylic acid, basic polymers of esters of polyacrylic acid, polymethacrylic acid and amino-alcohols, for example, their salts or quaternization products, polyacrylonitrile, polyvinyl acetate, as well as copolymers of such compounds, such as polyvinyl-pyrrolidone-vinyl acetate, are mentioned. As natural polymers, chitosan (deacetylated chitin) or chitosan derivatives may, for example, be used.

The aforementioned polymers may be used in the dyeing agent in amounts, customary for such agents, especially in an amount of about 1 to 5% by weight. The pH of the inventive shade fastener or color fastener preferably is 6 to 9.

For dyeing hair, the dyeing agent usually is applied on the hair in an amount, sufficient for dyeing the hair, of about 30 to 120 g, depending on the length of the hair, and allowed to act at about 15° to 45° C. for about 1 to 60 minutes and preferably for 5 to 30 minutes. Subsequently, the hair is rinsed thoroughly with water, optionally washed with a shampoo and subsequently dried.

The use of the dyeing agent with additional consolidation takes place in the well-known and usual manner by moistening the hair with the strengthener, putting it in place for the hair style and subsequently drying it.

The dyeing agents containing the 7-nitro-2, 1, 3-benzoxadiazole compounds and 7-nitro-2,1,3-benzthiadiazole compounds of formula (I) make possible an outstanding, uniform, intensive dyeing of keratin fibers (particularly human hair) under gentle and skin-compatible conditions. The dyeing is extremely resistant to shampooing light and sweat.

The following examples are intended to explain the object of the invention in greater detail, without limiting it.

EXAMPLES

Example 1

Synthesis of Sodium Salt of 4-(dicyanomethyl)-7-nitro-2,1,3-benzoxadiazole

4-Chloro-7-nitro-2,1,3-benzoxadiazole (0.5 g, 2.5 mmoles) is suspended in 13 mL of ethanol and 0.256 g (2.5 mmoles) of sodium carbonate are added. The reaction mixture is treated at room temperature (20°–25° C.) with 0.165 g (2.5 mmoles) of malonic acid dinitrile. After it has been heated for 3 hours at 50° C., the reaction mixture is concentrated in a rotary evaporator, treated with acetone and filtered. The filtrate is concentrated in the rotary evaporator under vacuum, the desired product precipitating as the hydrate with 1 mole of water.

The yield is 95% of the theoretical.

Melting point: >300° C.

ESI (neg.) mass spectrum: $M^-$—Na: 228 (100% relative intensity)

$^1$H-NMR (DMSO-D6, 500 MHz): δ=8.18 ppm (d; I=9.1 Hz; 1H; H—C(6)); 6.48 ppm (d; I=9.1 Hz; 1H; H—C(5))

$^{13}$C-NMR (DMSO-D6, 75.4 MHz): δ=146.3 ppm (C(2)); 144.2 ppm (C(3)); 142.1 ppm (C(4)); 133.8 ppm (C(6)); 118.3 ppm (CN); 118.1 ppm (CN); 108.1 ppm (C(5)); 50.7 ppm (C(7))

UV-Vis spectrum (EtOH): $\lambda_{max}$=570 nm (42647); 382 nm (8300); 254 nm (8763)

Elementary analysis: $C_9H_2N_5O_3*Na*H_2O$ (269.16)

|  | % C | % H | % N |
| --- | --- | --- | --- |
| calculated: | 40.16 | 1.50 | 26.02 |
| found: | 40.16 | 1.76 | 25.19 |

Example 2

Synthesis of the Sodium Salt of 4-(1-cyano-2-ethoxy-2-oxoethyl)-7-nitro-2,1,3-benzoxadiazole 4-Chloro-7-nitro-2,1,3-benzoxidiazole (1.0 g, 5 mmoles) is suspended in 25. mL of ethanol and 0.53 g (5 mmoles) of sodium carbonate are added. The reaction mixture is treated at room temperature (20° to 25° C.) with 0.57 g (5 mmoles) of ethyl cyanoacetate. After being heated for 6 hours at 50° C., the reaction mixture is concentrated in a rotary evaporator, treated with acetone and filtered. Subsequently the filtrate is evaporated in a rotary evaporator under vacuum.

The yield is 98% of the theoretical.

Melting point: 260° C. (dec.)

ESI (neg.) mass spectrum: $M^{31}$—Na: 275 (100% relative intensity)

$^1$H-NMR (DMSO-D6, 500 MHz): δ=8.11 ppm (d; I=9.3 Hz; 1H;H—C(6)); 7.89 ppm (d; I=9.3 Hz; 1H; H—C(5)); 4.15 ppm (q; I=7.0 Hz; 2 H; $CH_2$); 1.24 ppm (t; I=7.0 Hz; 3 H; $CH_3$)

UV-Vis spectrum (EtOH): $\lambda_{max}$=575 nm (38755); 389 nm (6539); 226 nm (8526)

Elementary analysis: $C_{11}H_8N_4O_5$*Na*(298.19)

|  | % C | % H | % N |
|---|---|---|---|
| calculated: | 44.31 | 2.37 | 18.79 |
| found: | 44.17 | 2.81 | 18.02 |

Example 3
Synthesis of the Sodium Salt of 4-(dicyanomethyl)-7-nitro-2,1,3-benzoxadiazole-N-oxide 4-Nitrobenzofurazan-3-oxide (0.91 g, 5 mmoles) is suspended in 15 mL of ethanol and 1.06 g (10 mmoles) of sodium carbonate are added. The reaction mixture is treated at room temperature (20° to 25° C.) with 0.33 g (5 mmoles) of malonic acid dinitrile. After being heated for 3 hours at 50° C., the reaction mixture is concentrated in a rotary evaporator, treated with acetone and filtered. Subsequently the filtrate is evaporated in a rotary evaporator under vacuum. After chromatography on silica gel (9:1 ethyl acetate/methanol), 0.41 g of the desired product are obtained in the form of a dark violet powder.

The yield is 31% of the theoretical.

Melting point: >250° C.

ESI (neg.) mass spectrum: M⁻—Na—O: 228 (100% relative intensity)

¹H-NMR (DMSO-D6, 500 MHz): δ=8.21 ppm (d; I=8.8 Hz; 1H; H—C(6)); 6.51 ppm (d; I=8.8 Hz; 1H; H—C(5))

UV-Vis spectrum (EtOH): $\lambda_{max}$=574 nm (34163); 384 nm (7485); 250 nm (9425)

Example 4
Synthesis of the Sodium Salt of 4-(dicyanomethyl)-7-nitro-2,1,3-benzthiadiazole 4-Nitro-2,1,3-benzothiadiazol (0.91 g, 5 mmoles) is dissolved in 15 mL of ethanol and 0.53 g (5 mmoles) of sodium carbonate are added. The reaction mixture is treated at room temperature (20° to 25° C.) with 0.33 g (5 mmoles) of malonic acid dinitrile. After being heated for 7 hours at 50° C., the reaction mixture is concentrated in a rotary evaporator, treated with methanol and filtered. Subsequently the filtrate is evaporated in a rotary evaporator under vacuum. After chromatography on silica gel (ethyl acetate), 0.4 g of the dark violet product are obtained.

The yield is 33% of the theoretical.

Melting point: 230° C.

ESI (neg.) mass spectrum: M⁻—Na: 244 (100% relative intensity)

¹H-NMR (DMSO-D6, 500 MHz): δ=8.33 ppm (d; I=9.1 Hz; 1H; H—C(6)); 6.71 ppm (d; I=9.1 Hz; 1H; H—C(5))

UV-Vis spectrum (EtOH): $\lambda_{max}$=574 nm (24028); 404 nm (7400); 312 nm (5040)

Examples 5 to 13
Synthesis of 7-nitro-2,1,3-benzoxadiazole or 7-nitro-2,1,3-benzthiadiazole Derivatives General Procedure An equimolar mixture of 7-nitro-2,1,3-benzoxadiazol or 7-nitro-2,1,3-benzthiadiazol derivatives of Formula (I) and the CH-active compound are suspended in ethanol and treated with 1 to 2 equivalents of sodium carbonate. After being heated for 3 hours at 50° C., the reaction mixture is concentrated in a rotary evaporator, treated with acetone and filtered and the filtrate is evaporated under vacuum in a rotary evaporator, the desired product precipitating. After purification by chromatography on silica gel or by recrystallization, the desired product is isolated in crystalline form.

The corresponding data are summarized in the following Table 1.

TABLE 1

| Example No. | 7-Nitro-2,1,3-benzoxadiazole or. 7-nitro-2,1,3-benzthiadiazole derivative | CH-active compound | Dye of general Formula (I) | Yield | MS ESI (neg.) 100% | Melting point | UV (ethanol) |
|---|---|---|---|---|---|---|---|
| 5 | 4-Chloro-7-nitro-2,1,3-benzoxadiazole 0.50 g (2.5 mmoles) | Barbituric acid 0.32 g (2.5 mmoles) | Sodium salt of 4-(dihydro-2,4,6(1H,5H)-pyrimidine-trione-5-yl)-7-nitro-2,1,3-benzoxadiazole | 5% | 290 (M⁻-Na) | >250° C. | 514 nm (4010) 328 nm (3072) 254 nm (7924) |
| 6 | 4-Chloro-7-nitro-2,1,3-benzoxadiazole 0.40 g (2.0 mmoles) | Pivaloyl acetonitrile 0.25 g (2.0 mmoles) | Sodium salt of 4-(1-cyano-3,3-dimethyl-2-oxobutyl)-7-nitro-2,1,3-benzoxadiazole | 16% | 287 (M⁻-Na) | 192° C. (dc) | 590 nm (28068) 384 nm (5934) 232 nm (10794) |
| 7 | 4-Chloro-7-nitro-2,1,3-benzoxadiazole 1.0 g (5.0 mmoles) | Dimethyl malonate 0.66 g (5.0 mmoles) | Sodium salt of 4-bis(methoxy-carbonyl)-7-nitro-2,1,3-benzoxadiazole | 10% | 294 (M⁻-Na) | Oil | 450 nm (sh, 1150) 330 nm (5150) |
| 8 | 4-Chloro-7-nitro-2,1,3-benzoxadiazole 0.50 g (2.5 mmoles) | 1-Phenyl-3-methyl-5-pyrazolone 0.44 g (2.5 mmoles) | Sodium salt of 4-(4,5-dihydro-3-methyl-1-phenyl-1H-pyrazole-5-one-4-yl)-7-nitro-2,1,3-benzoxadiazole | 41% | 336 (M⁻-Na) | >110° C./dc | 598 nm (10445) 446 nm (4557) 380 nm (4654) 250 nm (19106) |

TABLE 1-continued

| Example No. | 7-Nitro-2,1,3-benzoxadiazole or. 7-nitro-2,1,3-benzthiadiazole derivative | CH-active compound | Dye of general Formula (I) | Yield | MS ESI (neg.) 100% | Melting point | UV (ethanol) |
|---|---|---|---|---|---|---|---|
| 9 | 4-Chloro-7-nitro-2,1,3-benzoxadiazole 1.00 g (5.0 mmoles) | 4-Nitrobenzyl cyanide 0.81 g (5.0 mmoles) | Sodium salt of 4-(cyano-(4-nitrophenyl)-methyl)-7-nitro-2,1,3-benz-oxadiazole | 9% | 324 (M$^-$-Na) | >280° C. | 568 nm (19238) 420 nm (10110) 264 nm (12365) |
| 10 | 4-Nitro-2,1,3-benzoxadiazole-3-oxide 0.91 g (5.0 mmoles) | 2-Cyanacetamide 0.42 g (5.0 mmoles) | Sodium salt of 4-((aminocarbonyl)-cyano-methyl)-7-nitro-2,1,3-benz-oxadiazole-1-oxide | 5% | 246 (M$^-$-Na—O) | >280° C. | 580 nm (11546) 400 nm (3088) 220 nm (9271) |
| 11 | 4-Nitro-2,1,3-benzoxadiazole-3-oxide 0.91 g (5.0 mmoles) | Ethyl cyanoacetate 0.57 g (5.0 mmoles) | Sodium salt of 4-(1-cyano-2-ethoxy-2-oxoethyl)-7-nitro-2,1,3-benz-oxadiazole-1-oxide | 22% | 275 (M$^-$-Na—O) | 300° C. | 578 nm (32357) 390 nm (5701) 315 nm (1975) |
| 12 | 4-Nitro-2,1,3-benzothiazole 0.91 g (5.0 mmoles) | Ethyl cyanoacetate 0.57 g (5.0 mmoles) | Sodium salt of 4-(1-cyano-2-oxoethyl)-7-nitro-2,1,3-benz-thiadiazole | 20% | 291 (M$^-$-Na) | Oil | 580 nm (27502) 408 nm (6920) 310 nm (5706) 268 nm (9476) |
| 13 | 4-Nitro-2,1,3-benzothiazole 0.91 g (5.0 mmoles) | 4-Nitrobenzyl cyanide 0.81 g (5.0 mmoles) | Sodium salt of 4-(cyano-(4-nitrophenyl)-methyl)-7-nitro-2,1,3-benz-thiadiazole | 35% | 340 (M$^-$-Na) | >280° C. | 604 nm (8611) 446 nm (6322) 260 nm (14718) |

Examples 14 to 28

Hair Dye

| | |
|---|---|
| 2.5 mmoles | dye of Formula (I) of Table 2 |
| 5.0 g | ethanol |
| 2.0 g | decyl glucoside (Plantaren ® 2000 UP NP) |
| 0.2 g | disodium ethylenediaminetetraacetate acid hydrate |
| ad 100.0 g | water, fully desalinated |

The above dye solution is adjusted to the pH given in Table 2 by the addition of ammonia or citric acid.

The hair is dyed by applying an amount of dye, sufficient for the dyeing onto the hair. After a period of action of 30 minutes at 40° C. the hair is rinsed with lukewarm water and dried.

The dyeing results are summarized in the Table 2 below:

The L*a*b*measured color values, given in the examples, were determined with a Minolta, Type II Chromameter. The "L" value represents the brightness (that is, the lower the "L" value, the greater is the intensity of the color), whereas the "a" value is a measure of the red portion (the red portion varies with the value of "a"). The "b" value is a measure of the blue portion of the color (the more negative the value of "b", the greater is the blue portion).

| Example No. | Dye of Formula (I) | pH Value | Color | L*a*b* Measured Color Values |
|---|---|---|---|---|
| 14 | Sodium salt of 4-(dicyanomethyl)-7-nitro-2,1,3-benzoxadiazole (of Example 1) | 7.3 | deep violet | L = +25.17 a = +54.12 b = −24.03 |
| 15 | Sodium salt of 4-(dicyanomethyl)-7-nitro-2,1,3-benzoxadiazole (of Example 1) with copper(II)chloride | 3.8 | deep violet | L = +22.16 a = +25.99 b = −11.15 |
| 16 | Sodium salt of 4-(1-cyano-2-ethoxy-2-oxoethyl)-7-nitro-2,1,3-benzoxadiazole (of Example 2) | 5.4 | violet | L = +27.57 a = +27.27 b = +3.22 |
| 17 | Sodium salt of 4-(dicyanomethyl)-7-nitro-2,1,3-benzoxadiazole-N-oxide (of Example 3) | 7.2 | blue violet | L = +18.07 a = +26.87 b = −14.93 |
| 18 | Sodium salt of 4-(dicyanomethyl)-7-nitro-2,1,3-benzthiadiazole (of Example 4) | 7.2 | pink violet | L = +38.94 a = +50.44 b = −28.02 |

-continued

| Example No. | Dye of Formula (I) | pH Value | Color | L*a*b* Measured Color Values |
|---|---|---|---|---|
| 19 | Sodium salt of 4-(dihydro-2,4,6(1H,5H)-pyrimidine-trione-5-yl)-7-nitro-2,1,3-benzoxadiazole (of Example 5) | 3.0 | red | L = +28.15<br>a = +34.22<br>b = +3.31 |
| 20 | Sodium salt of 4-(1-cyano-3,3-dimethyl-2-oxobutyl)-7-nitro-2,1,3-benzoxadiazole (of Example 6) | 10.0 | blue | L = +20.82<br>a = +17.86<br>b = −15.88 |
| 21 | Sodium salt of 4-(bis(methoxycarbonyl)-7-nitro-2,1,3-benzoxadiazole (of Example 7) | 6.5 | orange red | L = +37.82<br>a = +41.64<br>b = +22.80 |
| 22 | Sodium salt of 4-(4,5-dihydro-3-methyl-1-phenyl-1H-pyrazole-5-one-4-yl)-7-nitro-2,1,3-benzoxadiazole (of Example 8) | 10.2 | turquoise blue | L = +27.15<br>a = −4.60<br>b = −16.72 |
| 23 | Sodium salt of 4(cyano-(4-nitrophenyl)-methyl)-7-nitro-2,1,3-benzoxadiazole (of Example 9) | 4.85 | brown gray | L = +43.2<br>a = +7.65<br>b = +0.09 |
| 24 | Sodium salt of 4-((aminocarbonyl)-cyano-methyl)-7-nitro-2,1,3-benzoxadiazole-1-oxide (of Example 10) | 6.4 | violet | L = +23.35<br>a = +36.90<br>b = −2.83 |
| 25 | Sodium salt of 4-((aminocarbonyl)-cyano-methyl)-7-nitro-2,1,3-benzoxadiazole-1-oxide (of Example 10) | 2.4 | violet black | L = +18.61<br>a = +19.49<br>b = +0.79 |
| 26 | Sodium salt of 4-(1-cyano-2-ethoxy-2-oxoethyl)-7-nitro-2,1,3-benzoxadiazole-1-oxide (of Example 11) | 6.6 | blue violet | L = +22.68<br>a = +38.55<br>b = −19.99 |
| 27 | Sodium salt of 4-(1-cyano-2-ethoxy-2-oxoethyl)-7-nitro-2,1,3-benzthiadiazole (of Example 12) | 7.0 | blue violet | L = +22.67<br>a = +27.77<br>b = −20.98 |
| 28 | Sodium salt of 4-(cyano-(4-nitrophenyl)-methyl)-7-nitro-2,1,3-benzthiadiazole (of Example 13) | 4.7 | light gray | L = +47.5<br>a = −2.29<br>b = +6.15 |

Unless stated otherwise, all percentages given represent percentages by weight.

What is claimed is:

1. A 7-nitro-2,1,3-benzoxadiazole compound of formula (I):

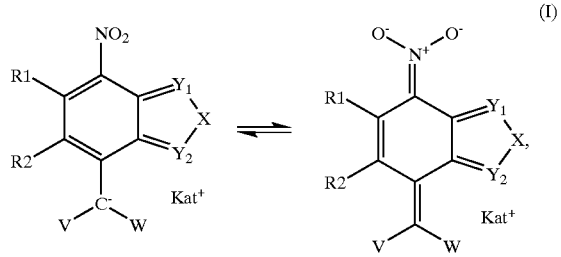

wherein X is oxygen, $Y_1$ and $Y_2$ each represent a nitrogen atom;

R1 and R2 are the same or different and, independently of one another, each represent hydrogen, a halogen atom, a $(C_1-C_4)$-alkyl group, a substituted $(C_1-C_4)$-alkyl group substituted with a halogen atom, a $(C_1-C_4)$-alkoxy group, a nitro group or an $NR^aR^b$ group, the $R^a$ and $R^b$ are the same or different and, independently of one another, each represent hydrogen, a $(C_1-C_4)$-alkyl group, an optionally substituted, aromatic carbocyclic group or a $(C_1-C_4)$-alkane carbonyl group V represents hydrogen, an aliphatic group, an aromatic isocyclic group, a cyano group or a carbonyl function (CO)—R3, wherein R3 represents hydrogen, a hydroxy group, a $(C_1-C_4)$-alkoxy group, an amino group, a $(C_1-C_4)$-alkylamino group, a $(C_1-C_6)$-alkyl group or an aryl group;

W represents a cyano group or a carbonyl function (CO)—R4, R4 representing hydrogen, a hydroxy group, a $(C_1-C_4)$-alkoxy group, an amino group, a $(C_1-C_4)$-alkylamino group, a $(C_1-C_6)$-alkyl group or an aryl group; and Kat$^+$ represents an alkali cation, an alkaline earth cation, a quaternary ammonium group, a quaternary phosphonium group or a sulfonium group.

2. The compound as defined in claim 1, wherein said R1 and said R2, independently of one another, each represent said hydrogen, said halogen atom, said $(C_1-C_4)$-alkyl group or said nitro group.

3. A 7-nitro-2,1,3-benzoxadiazole compound selected from the group consisting of 4-(dicyanomethyl)-7-nitro-2,1,3-benzoxadiazole sodium salt, 4-(1-cyano-2-ethoxy-2-oxoethyl)-7-nitro-2,1,3-benzoxadiazole sodium salt, 4-(dicyano-methyl)-7-nitro-2,1,3-benzoxadiazole-N-oxide sodium salt, 4-(1-cyano-3,3-dimethyl-2-oxobutyl)-7-nitro-2,1,3-benzoxadiazole sodium salt, 4-(bis(methoxycarbonyl)-7-nitro-2,1,3-benzoxadiazole sodium salt, 4-(cyano-(4-nitrophenyl)-methyl)-7-nitro-2,1,3-benzoxadiazole sodium salt, 4-((aminocarbonyl)-cyano-methyl)-7-nitro-2,1,3-benzoxadiazole-1 -oxide sodium salt, 4-(1-cyano-2-ethoxy-2-oxoethyl)-7-nitro-2,1,3-benzoxadiazole-1-oxide sodium salt, 4-(carboxy-cyanomethyl)-7-nitro-2,1,3-benzoxadiazole sodium salt, 4-(2-ethoxy-1-nitro-2-oxoethyl)-7-nitro-2,1,3-benzoxadiazole sodium salt, 4-((amino-carbonyl)cyanomethyl)-7-nitro-2,1,3-benzoxadiazole sodium salt, 4-(1-cyano-2-oxo-2-phenylethyl-7-nitro-2,1,3-benzoxadiazole sodium salt and 4-(cyano-(2-nitrophenyl)-methyl)-7-nitro-2,1,3-benzoxadiazole sodium salt.

4. An agent for dyeing keratin fibers, wherein the agent contains at least one 7-nitro-2,1,3-benzoxadiazole compound of formula (I):

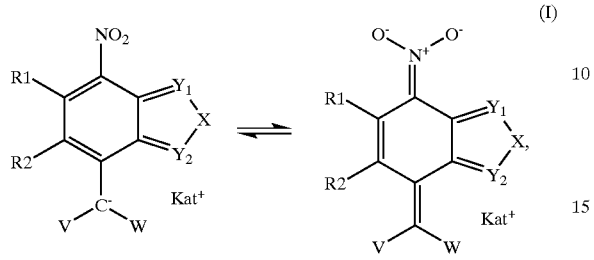

wherein X is oxygen;

$Y_1$ and $Y_9$ each represent a nitrogen atom.

$R_1$ and $R_2$ are the same or different and, independently of one another, each represent hydrogen, a halogen atom, a ($C_1$–$C_4$)-alkyl group substituted ($C_1$–$C_4$)-alkyl group substituted with a halogen atom, a ($C_1$–$C_4$)-alkoxy group, a nitro group or an $NR^aR^b$ group, the $R^a$ and $R^b$ are the same or different and, independently of one another, each represent hydrogen, a ($C_1$–$C_4$)-alkyl group, an optionally substituted, aromatic carbocyclic group or a ($C_1$–$C_4$)-alkane carbonyl group;

V represents hydrogen, an aliphatic group, an aromatic isocyclic group, a cyano group or a carbonyl function (CO)—R3, wherein R3 represents hydrogen, a hydroxy group, a ($C_1$–$C_4$)-alkoxy group, an amino group, a ($C_1$–$C_4$)-alkylamino group, a ($C_1$–$C_6$)-alkyl group or an aryl group;

W represents a cyano group or a carbonyl function (CO)—R4, R4 representing hydrogen, a hydroxy group, a ($C_1$–$C_4$)-alkoxy group, an amino group, a ($C_1$–$C_4$)-alkylamino group, a ($C_1$–$C_6$)-alkyl group or an aryl group; and $Kat^+$ represents an alkali cation, an alkaline earth cation, a quaternary ammonium group, a quaternary phosphonium group or a sulfonium group.

5. The agent as defined in claim 4, containing from 0.01 to 10 percent by weight of said at least one 7-nitro-2,1,3-benzoxadiazole compound of formula (I).

6. The agent as defined in claim 4, containing at least one substantive dye ingredient selected from the group consisting of anionic dyes, cationic dyes, nonionic dyes, amphoteric dyes, nitro dyes azo dyes, anthra-quinone dyes and dispersion dyes.

7. The agent as defined in claim 4, containing at least one polymer selected from the group consisting of natural polymers, synthetic polymers and modified polymers of natural origin and wherein said at least one polymer is a shade fastener or color fastener.

8. The agent as defined in claim 4, consisting of a hair-dyeing agent.

9. A method of dyeing hair, said method comprising the steps of:

a) providing an agent for dyeing hair containing at least one 7-nitro-2,1,3-benzoxadiazole compound of formula (I):

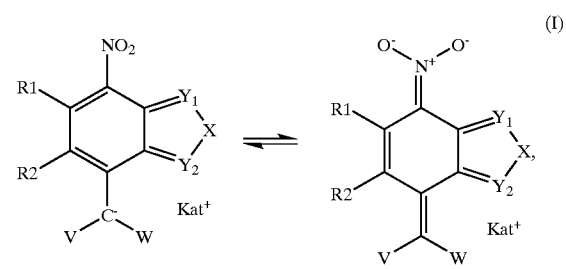

wherein X is oxygen;

$Y_1$ and $Y_2$ each represent a nitrogen atom;

R1 and R2 are the same or different and, independently of one another, each represent hydrogen, a halogen atom, a ($C_1$–$C_4$)-alkyl group, a substituted ($C_1$–$C_4$)-alkyl group substituted with a halogen atom, a ($C_1$–$C_4$)-alkoxy group, a nitro group or an $NR^aR^b$ group, the $R^a$ and $R^b$ are the same or different and, independently of one another, each represent hydrogen, a ($C_1$–$C_4$)-alkyl group, an optionally substituted, aromatic carbocyclic group or a ($C_1$–$C_4$)-alkane carbonyl group;

V represents hydrogen, an aliphatic group, an aromatic isocyclic group, an aromatic heterocyclic group, a cyano group or a carbonyl function (CO)—R3, wherein R3 represents hydrogen, a hydroxy group, a ($C_1$–$C_4$)-alkoxy group, an amino group, a ($C_1$–$C_4$)-alkylamino group, a ($C_1$–$C_8$)-alkyl group or an aryl group;

W represents a cyano group or a carbonyl function (CO)—R4, R4 representing hydrogen, a hydroxy group, a ($C_1$–$C_4$)-alkoxy group, an amino group, a ($C_1$–$C_4$)-alkylamino group, a ($C_1$–$C_6$)-alkyl group or an aryl group; and $Kat^+$ represents an alkali cation, an alkaline earth cation, a quaternary ammonium group, a quaternary phosphonium group or a sulfonium group;

b) applying the agent to the hair in an amount sufficient for the dyeing of the hair, depending on an amount of the hair to be dyed;

c) allowing the agent applied In step b) to act on the hair at from 15° to 45° C. for about 1 to 60 minutes; and d) then rinsing the hair, optionally washing the hair with a shampoo and subsequently drying the hair.

* * * * *